(12) United States Patent
Nösel

(10) Patent No.: US 6,708,948 B2
(45) Date of Patent: Mar. 23, 2004

(54) ENDOSCOPE STOPCOCK WITH A DETENT DEVICE

(75) Inventor: Bernd Nösel, Lütjensee (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 101 days.

(21) Appl. No.: 10/154,230

(22) Filed: May 23, 2002

(65) Prior Publication Data

US 2002/0179878 A1 Dec. 5, 2002

(30) Foreign Application Priority Data

May 30, 2001 (DE) .......................... 101 26 540

(51) Int. Cl.$^7$ ................................ F16K 5/00
(52) U.S. Cl. ........................ 251/288; 251/312
(58) Field of Search ................. 251/309, 312, 251/904, 304, 288, 286

(56) References Cited

U.S. PATENT DOCUMENTS

| | | | | |
|---|---|---|---|---|
| 1,966,807 A | * | 7/1934 | Sweet et al. ............... | 251/314 |
| 3,779,513 A | * | 12/1973 | Levine ...................... | 251/309 |
| 4,614,203 A | * | 9/1986 | Russo ....................... | 251/309 |
| 5,337,780 A | * | 8/1994 | Kee .......................... | 251/904 |

FOREIGN PATENT DOCUMENTS

DE  198 19 814 C1  6/1999

* cited by examiner

*Primary Examiner*—John Bastianelli
(74) *Attorney, Agent, or Firm*—Rankin, Hill, Porter & Clark LLP

(57) ABSTRACT

A stopcock for controlling ducts in a medical endoscopes passing flux media, including a housing made of a hard material and rotatably receiving a conical plug in a conical seat crossed by a duct. The housing subtends, in the direction of the axis of rotation and beyond the larger opening of the conical seat, a bearing collar which supports a rotary body that is rotatable about the axis of rotation. The rotary body is fitted outside said housing with a handle and is rotationally coupled with the plug. The rotary body is axially displaceable and biased by a spring relative to the plug and is further fitted with a radially elastic detent device, which in the assembled state of the stopcock is configured inside the housing. The rotary body, by operation of the detent device, acts in a locking manner against the spring action on the bearing collar. The rotary body includes a prefabricated rupture site that, following deliberate rupture, exposes the snap-in device.

2 Claims, 1 Drawing Sheet

ENDOSCOPE STOPCOCK WITH A DETENT DEVICE

BACKGROUND OF THE INVENTION

1. Field of the Invention

The invention generally relates to a stopcock for controlling ducts in a medical endoscope for passing flux media.

2. Description of Related Art

Stopcocks on endoscopes control flux media such as gas or irrigation liquids flowing through ducts in the endoscope. In earlier designs, a plug is secured by a screw on the stopcock housing.

The German patent document 198 19 814 C1 discloses a design of this kind. The stopcock housing is made of metal and is permanently affixed to the endoscope, for instance by welding. To take care of friction and to assure sealing, the plug is made of an appropriate plastic. The rotary body, together with its handle, is also made of plastic and, by means of a detent device, snaps into the housing and thereby facilitates assembly and makes the stopcock manufacture more economical with respect to earlier designs comprising screw connections.

Because the detent device seated on the rotary body is configured within the housing when assembled, it is inaccessible following appropriate snap-in insertion and, thereafter, will also be undetachable. If defects arise in the stopcock, especially when the conical element has suffered wear, the stopcock must be exchanged as a whole, and the entailed repair is unusually elaborate. Accordingly, there exists a need in the art for an improved stopcock design that facilitates and simplifies repair and maintenance.

SUMMARY OF THE INVENTION

An object of the present invention is to create a stopcock that permits simpler and more economical repairs.

In accordance with the present invention, the rotary body includes a prefabricated rupture site that, after being deliberately ruptured, allows access to the detent device. To undertake repairs, the predetermined rupture site is broken by forcing the rotary body's handle. Thereafter, the detent device is accessible and it may be unlocked and removed using an appropriate tool. Next, the remainder of the rotary body together with the detent element, the spring and plug, may be removed and replaced by new parts. During this procedure the stopcock housing may remain on the endoscope while the elaborate steps heretofore required to change the housing now are eliminated.

The detent device may be designed in the manner of the cited German patent document 198 19 814 C1. However, in accordance with further features of the present invention, the detent device is a snap ring within a circumferential groove of the rotary body. The circumferential groove is deep enough to act as the prefabricated rupture site. The functions of this design are therefore attained in very simple manner.

BRIEF DESCRIPTION OF THE DRAWING

These and further features of the invention will be apparent with reference to the drawing, which illustratively and schematically shows a cross-section of the stopcock of the present invention.

DETAILED DESCRIPTION OF THE PREFERRED EMBODIMENT

Figure 1:
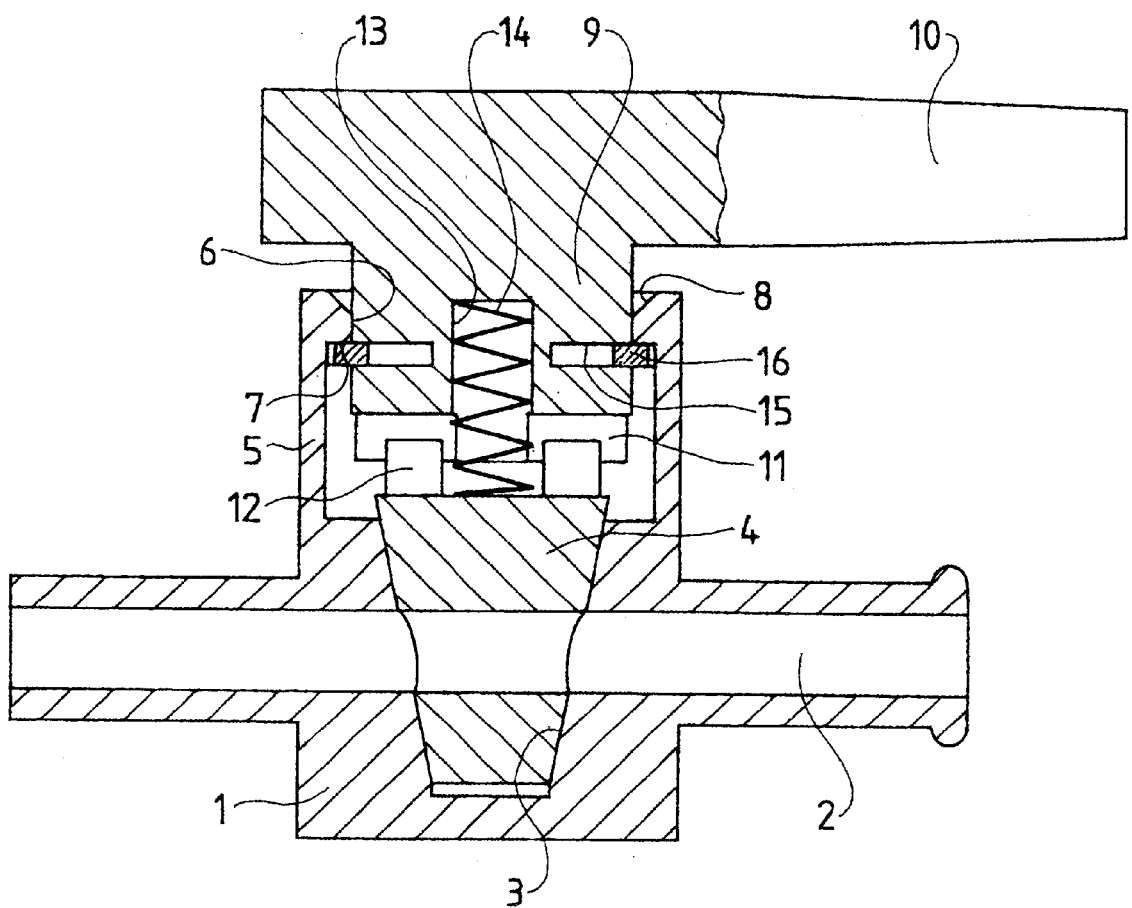

The shown stopcock has a housing 1 that is crossed by a duct 2. The duct 2 crosses or intersects a conical seat 3 receiving a rotary conical plug 4. The housing 1 is made of a hard material, preferably a metal. The conical plug 4 is made of a softer material, preferably an appropriate plastic.

Seen in the axial direction of the conical seat 3 and beyond the larger opening of this conical seat, the housing 1 constitutes a tubular wall 5, which, at its end away from the conical seat 3, tapers into an annular bearing collar 6. In the direction toward the conical seat 3, the bearing collar 6 constitutes an annular stop edge 7. The bearing collar 6 is fitted with an insertion bevel 8 facing toward the outside.

A rotary body 9, which is also made of plastic and has appropriate properties and moderately mechanically yielding, is braced in the shown assembled position within the bearing collar 6 and is rotatable about the axis of the conical seat 3. The rotary body 9 is fitted at its end away from the housing 1 with an asymmetrical handle 10 that is used to rotate the rotary body 9.

At its end facing the conical plug 4, the rotary body 9 comprises a transverse groove 11 that receives two protrusions 12 affixed on the end surface of the conical plug 4 that faces the rotary body 9. As shown by the drawing, the protrusions 12 allow some longitudinal shift toward the axis of rotation between the conical plug 4 and the rotary body 9, while nevertheless securing the rotational connection between these two parts. The longitudinally displaceable rotational coupling of these two parts may also be implemented in another manner. For example, the transverse groove may be fitted into the plug and the protrusions may be configured at the rotary body.

A blind borehole 13 situated on the axis of rotation extends into the rotary body 9 from its end surface facing the conical plug 4 and receives a helical spring 14. The helical spring 14 rests, on one hand, on the bottom of the blind bore 13 and, on the other hand, on the end surface of the conical plug 4.

In the shown assembled configuration, a circumferential groove 15 of appropriate depth is formed in the rotary body 9. The groove 15 is situated at the level of the stop edge 7 of the bearing collar 6 and receives and holds a snap ring 16.

The shown design is assembled by first inserting the conical plug 4 into the housing 1 via the opening at the top of the housing. Thereafter, the rotary body 9 together with the snap ring 16 and helical spring 14 are axially pressed into the housing at an appropriate rotational position allowing the protrusions 12 to enter the transverse groove 11. In the process, the snap ring 16, which when unstressed is larger than the circumference of the rotary body 9, is resiliently compressed at the insertion bevel 8. Once the snap ring 16 has moved past the bearing collar 6, it will expand behind the stop edge 7. The rotary body 9, now rotationally coupled to the conical plug 4, is rotationally supported in the housing 1 and is kept in the locked position in the housing while being biased by the helical spring 14.

As shown, the detent device in the form of the shown snap ring 16 now is located inside the tubular wall 5 of the housing 1 and, hence, is inaccessible from the outside.

If the shown stopcock must be disassembled, then the housing 1, on one hand, and the handle 10, on the other hand, shall be actuated and force shall be applied to the rotary body 9, which thereby will be broken off the assembly at its prefabricated rupture site constituted by the circumferential groove 15. Thereafter, the detent device embodied in the snap ring 16 is easily accessible from the outside and may be detached using a suitable tool, such as snap-ring tongs. The remaining parts inside the housing may be removed through the opening of the housing 1 at the bearing collar 6 and be replaced with new parts in relation to the above discussed assembly procedure.

The prefabricated rupture site may also assume other forms. Instead of the shown annular groove 15, the rotary body 9 also may be weakened in other ways. For instance, the rupture site may be constituted by adjoining parts that are connected at their junction by a connecting means that is subsequently easily torn off.

As regards other, similar embodiments of the stopcock such as disclosed in the German patent document 198 19 814 C1, other sites also prepared for a rupture exposing the locking device may be provided in the rotary body to facilitate disassembly.

What is claimed is:

1. A stopcock for controlling ducts in medical endoscopes passing flux media, comprising a housing (1) made of a hard material and rotatably receiving a conical plug (4) in a conical seat (3) crossed by a duct (2), said housing subtending, in the direction of an axis of rotation and beyond a larger opening of the conical seat (3), a bearing collar (6) that supports a rotary body (9) that is rotatable about the axis of rotation, said rotary body being fitted outside said housing with a handle (10) and being rotationally coupled with the plug, said rotary body being axially displaceable and biased by a spring relative to said plug and further being fitted with a radially elastic detent device (16), which in the assembled state of said stopcock, is configured inside the housing, said rotary body (9) by operation of said detent device (16) acting in a locking manner against the spring action on said bearing collar (6), wherein the rotary body (9) is fitted with prefabricated rupture site (15) that, following deliberate rupture, exposes the detent device (16).

2. The stopcock as claimed in claim 1, wherein the prefabricated rupture site is formed as a circumferential groove (15) holding a detent device, which is formed as a snap ring (16).

* * * * *